(12) United States Patent
Cavallini et al.

(10) Patent No.: US 8,415,392 B2
(45) Date of Patent: Apr. 9, 2013

(54) COMBINED USE OF L-CARNITINE, ACETYLE L-CARNITINE AND PROPIONYL L-CARNITINE FOR THE TREATMENT OF OLIGOASTHENOTERATOSPERMIA

(75) Inventors: Giorgio Cavallini, Rome (IT); Giulio Biagiotti, Rome (IT); Aleardo Koverech, Rome (IT); Francesca Sardelli, Rome (IT)

(73) Assignee: Sigma-Tau Industrie Farmaceutiche Riunite, S.p.A., Rome (IT)

( * ) Notice: Subject to any disclaimer, the term of this patent is extended or adjusted under 35 U.S.C. 154(b) by 210 days.

(21) Appl. No.: 12/230,992

(22) Filed: Sep. 9, 2008

(65) Prior Publication Data

US 2009/0012169 A1   Jan. 8, 2009

Related U.S. Application Data

(62) Division of application No. 10/510,450, filed as application No. PCT/IT03/00214 on Apr. 8, 2003, now abandoned.

(30) Foreign Application Priority Data

Apr. 9, 2002  (IT) .............................. RM2002A0194

(51) Int. Cl.
  *A61K 31/195*   (2006.01)
(52) U.S. Cl. ..................................................... 514/561
(58) Field of Classification Search .................. 514/561
  See application file for complete search history.

(56) References Cited

U.S. PATENT DOCUMENTS

| 6,090,848 A | 7/2000 | Cavazza |
| 6,255,346 B1 | 7/2001 | Fassi et al. |

FOREIGN PATENT DOCUMENTS

| EP | 0 539 336 A | 4/1993 |
| WO | WO 98/43499 A | 10/1998 |
| WO | WO 99/17623 A | 4/1999 |
| WO | WO 99/18967 | 4/1999 |
| WO | WO 99/27925 A | 6/1999 |
| WO | WO02/058693 | * 8/2002 |
| WO | WO 03/066573 | 8/2003 |

OTHER PUBLICATIONS

Costa, M., et al., "L-carnitine in idiopathic asthenozoospermia: a multicenter study", *Andrologia*, 26:155-159 (1994).
Moncada, Mi., et al., "Effect of acetylcarnitine treatment in oligoasthenospermic patients", *ACTA Europaea Fertilitatis*, 23(5):221-224 (1992).

* cited by examiner

*Primary Examiner* — San-Ming Hui
(74) *Attorney, Agent, or Firm* — Lucas & Mercanti, LLP

(57) ABSTRACT

L-carnitine, acetyl L-carnitine and propionyl L-carnitine inner salts, or their pharmaceutically acceptable salts, are used in combination to treat oligoasthenoterosperia including oligospermia, asthenospermia, and teratospermia.

29 Claims, No Drawings

COMBINED USE OF L-CARNITINE, ACETYLE L-CARNITINE AND PROPIONYL L-CARNITINE FOR THE TREATMENT OF OLIGOASTHENOTERATOSPERMIA

This application is a divisional of application Ser. No. 10/510,450 filed Jan. 7, 2005 now abandoned which in turn is the US national phase of international application PCT/IT03/00214 filed Apr. 8, 2003 which designated the U.S. and claims benefit of Italian RM2002A000194 dated Apr. 9, 2002, the entire content of which is hereby incorporated by reference.

The invention described herein relates to the use of L-carnitine, acetyl L-carnitine and propionyl L-carnitine, in combination, for the preparation of a medicine for the treatment of oligoasthenoteratospermia of any origin: inflammatory, idiopathic, hormonal, or associated with varicocele.

BACKGROUND OF THE INVENTION

The final common pathway of all these forms of infertility is the local accumulation of oxygen free radicals (Pasqualotto F. F. et al., Fertil. Steril. 73:459-464, 1999). To combat this accumulation antioxidant drugs can be used.

Most of the antioxidants currently available on the pharmaceutical market (vitamin E, glutathione, NADH) act in a manner unrelated to the Krebs cycle, and therefore in a manner related solely to the drug dosage and not to cell metabolism.

The substantial topographical and temporal heterogeneousness (within the same testicle) of human spermatogenesis (Silber S. J., Clin. Obstet. Gynaecol. 43:843-888, 1999) makes it impossible to establish a "fixed" dosage of antioxidants, since this would lead to over- and underdosing.

An excessive lowering of oxygen free radicals leads to inhibition of the acrosome and capacitation reaction of the spermatozoa (Ochendorf F. R., Hum. Reprod. Update. 5:399-402, 1999), whereas too high a concentration leads to morphological abnormalities of the spermatozoon itself (Gattuccio F., et. al., Varicocele 2000, Cofese Editore, Palermo 2000).

In Human Reprod. 13:3090-3093, 1998, a semiquantitative scoring system has been proposed based on US Doppler results to distinguish between obstructive and non-obstructive azoospermias.

In Human. Reprod. 15:2554-2558, 2000, it is reported that the transmediastinic testicular artery has a significantly greater resistivity index in non-obstructive azoospermic subjects than in controls and in oligoasthenospermic subjects.

In Fertil. Steril. 75:1088-1094, 2001, it is reported that the pulsatility index of the testicular artery is higher in obstructive than in non-obstructive azoospermia.

In J. Urol. 163:135, 2000, it is reported that intratesticular blood flow and blood flow rate are significantly lower in subjects with arrested maturation of spermatogenesis, that is to say with hypoplasia of the germ cells.

The spermatozoa are produced in the testicles and undergo post-gonadal maturation in the epididymis in order to acquire their fertilising capacity.

In plasma, high-molecular-weight proteins and small molecules such as the free carnitines facilitate the maturation of the gametes into competent, functional cells.

Epididymal L-carnitine, which comes from the plasma, has a beneficial effect on the spermatozoa. It passes into the spermatozoa by passive diffusion and is acetylated only in mature spermatozoa.

The relationship between the endogenous pool of free and acetylated carnitines and the progressive percentage of sperm motility indicate a more important metabolic function related to flagellar movement.

Thus, the start of sperm motility, in the epididymis, is probably independent of the carnitine system, while the energy properties of acetyl L-carnitine are relevant in "energy crisis" situations.

The accumulation of free carnitines in the cytoplasm in mature spermatozoa has to be regarded as a protective form of the mitochondrial metabolism which is useful for the survival of these isolated cells.

The use of L-carnitine, acetyl L-carnitine and propionyl L-carnitine in combination is already known.

In European patent EP 0 973 415, a dietetic composition is described consisting of L-carnitine, acetyl L-carnitine and propionyl L-carnitine, which is useful for athletes subject to intense physical effort, or for asthenic individuals.

In patent application WO 99/17623, a dietetic composition is described consisting of L-carnitine, acetyl L-carnitine and propionyl L-carnitine for the treatment of alcohol withdrawal syndrome.

Also known is the use of L-carnitine and of the alkanoyl L-carnitines for the treatment of male infertility.

In Drugs Exptl. Clin. Res. XXI(4):157-159, 1995, it is reported that the administration of L-carnitine, in a group of patients with idiopathic asthenospermia, improves sperm motility and increases the sperm count in 37 out of 47 patients treated.

In Dermatol. Monatschr. 169:572-575, 1983, the same results are confirmed.

In Andrologia, 26:155-159, 1994, it is reported that the administration of L-carnitine in infertile patients brings about a significant improvement of both a quantitative and qualitative nature in sperm motility.

In Fertilität 4.1-4, 1988, it is reported that L-carnitine therapy in infertile patients brings about an increase in carnitine levels in the spermatozoa and at the same time an increase in sperm motility and sperm count.

Loumbakis P., et al. (12th Congress of the European Association of Urology, Paris, 1-4 Sep., 1996) report preliminary data indicating that the administration of L-carnitine may have a positive effect on sperm quality.

In Acta Eur. Fertil. 23(5):221-224, 1992, it is reported that the use of acetyl L-carnitine in patients with idiopathic oligoastheno-spermia has no effect upon sperm density, but induces a progressive increase in sperm motility.

In U.S. Pat. No. 6,090,848, it is reported that the combination of L-carnitine and acetyl L-carnitine is useful for the treatment of oligoasthenoteratospermia.

The above-mentioned known compounds are certainly to be regarded as good therapeutic agents, but nevertheless present a number of disadvantages.

In fact, as mentioned above, in Drugs Exptl. Clin. Res. XXI (4):157-159, 1995, it is reported that the administration of L-carnitine to a group of patients with idiopathic oligoasthenoteratospermia improves the sperm count and increases sperm motility in 37 out of 47 patients treated, whereas, in Acta Eur. Fertil. 23(5):221-224, 1992, it is reported that the use of acetyl L-carnitine in patients with idiopathic oligoasthenospermia has no effect upon sperm density.

The combination described in U.S. Pat. No. 6,090,848, which is to be regarded as the best one known to date, was used as a reference compound during the study of the activity of the composition according to the present invention. The results obtained, reported here below, confirmed the activity of the composition described in U.S. Pat. No. 6,090,848, but also demonstrated, surprisingly and unexpectedly, that the combination according to the present invention is more active than the composition described in U.S. Pat. No. 6,090,848.

In the medical field, there is still a strongly perceived need for the availability of compositions useful for the treatment of oligoasthenoteratospermia, which do not present the disadvantages of the above-mentioned known compounds, or which improve the results obtained with the best of the known compositions currently in use.

BRIEF SUMMARY OF THE INVENTION

It has now been found that the use of L-carnitine, acetyl L-carnitine and propionyl L-carnitine or of one of their pharmaceutically acceptable salts, in combination, has proved capable of exerting a surprising synergistic effect in the treatment of all forms of oligoasthenoteratospermia.

One object of the present invention therefore is the use of L-carnitine, acetyl L-carnitine and propionyl L-carnitine inner salts or their pharmaceutically acceptable salts for the preparation of a medicine for the treatment of oligoasthenoteratospermia.

A further object of the present invention is the use of L-carnitine, acetyl L-carnitine and propionyl L-carnitine inner salts or their pharmaceutically acceptable salts, for the preparation of a medicine for the treatment of oligospermia.

A further object of the present invention is the use of L-carnitine, acetyl L-carnitine and propionyl L-carnitine inner salts or their pharmaceutically acceptable salts, for the preparation of a medicine for the treatment of asthenospermia.

A further object of the present invention is the use of L-carnitine, acetyl L-carnitine and propionyl L-carnitine inner salts or their pharmaceutically acceptable salts, for the preparation of a medicine for the treatment of teratospermia.

A further object of the present invention is the use of L-carnitine, acetyl L-carnitine and propionyl L-carnitine or their pharmaceutically acceptable salts, for the preparation of a nutritional composition for the treatment of oligoasthenoteratospermia.

A further object of the present invention is the use of L-carnitine, acetyl L-carnitine and propionyl L-carnitine or their pharmaceutically acceptable salts, for the preparation of a nutritional composition for the treatment of oligospermia.

A further object of the present invention is the use of L-carnitine, acetyl L-carnitine and propionyl L-carnitine or their pharmaceutically acceptable salts, for the preparation of a nutritional composition for the treatment of asthenospermia.

A further object of the present invention is the use of L-carnitine, acetyl L-carnitine and propionyl L-carnitine or their pharmaceutically acceptable salts, for the preparation of a nutritional composition for the treatment of teratospermia.

DETAILED DESCRIPTION OF THE INVENTION

It has been found that the combination according to the present invention is more active than the combination of L-carnitine and acetyl L-carnitine mentioned above, in improving both sperm count and sperm motility in man.

The L-carnitine, acetyl L-carnitine and propionyl L-carnitine can be in any form suitable for oral or parenteral administration in man.

L-carnitine, acetyl L-carnitine and propionyl L-carnitine can be formulated together, as a mixture, or can be formulated separately (packaged separately), using known methods. L-carnitine, acetyl L-carnitine and propionyl L-carnitine can be administered to an individual either when formulated in a mixture or when formulated in separate packs.

On the basis of various factors, such as the concentration of the active ingredients or the patient's condition, the combination according to the present invention can be marketed as a health food supplement, a nutritional supplement, or as a therapeutic product on sale with or without the need for a medical prescription.

According to the present invention, the molar ratio of L-carnitine to acetyl L-carnitine and propionyl L-carnitine or of one of their pharmaceutically acceptable salts ranges from 2.48:0.098:0.092 to 0.186:0.98:0.92.

Alternative molar ratios include the molar ratios ranging from 2.48:0.49:0.46 to 0.62:0.49:0.46.

Alternative molar ratios include the molar ratios ranging from 2.48:0.98:0.92 to 1.24:0.49:0.23.

The combination preparation according to the present invention, when in unit dosage form, contains from 4.0 g to 0.30 g of L-carnitine inner salt, from 0.20 to 2.0 g of acetyl L-carnitine inner salt and from 0.20 g to 2.0 g of propionyl L-carnitine inner salt, or an equimolar amount of one of their pharmaceutically acceptable salts.

The preferred combination preparation, in unit dosage form, contains 2 g of L-carnitine inner salt, 1 g of acetyl L-carnitine inner salt and 0.5 g of propionyl L-carnitine inner salt, or an equimolar amount of one of their pharmaceutically acceptable salts.

It has been found, however, that, although the daily dose of the above-mentioned active ingredients to be administered depends on the patients age, weight and condition, using professional experience it is generally advisable to administer, in a single dose or in multiple doses, from 0.3 to 4.0 g/day approx. of L-carnitine, from 0.20 to 2.0 g/day approx. of acetyl L-carnitine, and from 0.20 to 2.0 g/day approx. of propionyl L-carnitine, or an equimolar amount of one of their pharmaceutically acceptable salts.

Larger doses can be administered thanks to the extremely low toxicity of said active ingredients.

Reported here below is a clinical trial conducted in order to assess whether or not the combination according to the present invention improves sperm motility as compared to combined therapy with L-carnitine plus acetyl L-carnitine.

The patients recruited had to fulfill the following inclusion/exclusion criteria.

Inclusion criteria: young infertile males with asthenozoospermia recognised as being the sole cause of infertility over the preceding period of at least two years; the semen criteria that had to be fulfilled in at least two samples were: sperm concentration (M/ml) from 10 to 20, motility (%)>20<40 at 2 hours, rapid linear progression (%)<20 at 2 hours. The patients were subjected to history taking, bilateral scrotal echo-colour Doppler, physical examination, hormone assays (free and total testosterone, FSH, ML, 17 beta oestradiol, progesterone, prolactin), and a spermiogram (WHO 1999).

Exclusion criteria: acute genital inflammation, sperm concentration <5,000,000/ml. All patients gave their informed consent for participation in this open trial. In all, the patients examined were 8 patients with varicocele (6 grade II, 2 grade III), 12 patients with chronic inflammation of the sex glands, 12 patients with varicocele (8 grade II, 4 grade III)+chronic inflammation of the sex glands, 25 with cryptogenetic oligoasthenospermia, 2 with hypogonadotropic hypogonadism, 1 with hyperprolactinaemia, 4 with a history of surgery (unilateral cryptorchidia in 3 cases, bilateral in 1 case) and 2 with bilateral testicular trauma.

Semen was obtained by masturbation after at least 4 days of sexual abstinence. Semen samples were analysed within one hour of ejaculation for all parameters, using the standard methods recommended by the WHO (1987). Sperm motility was studied using a computerised motility analyser on at least two samples.

Semen analysis and the motility assessment were carried out before treatment with the study compounds and after 4 months' treatment with the latter.

L-carnitine was administered at the dose of 2 g/day (2×500 mg tablets twice daily, after lunch) for 4 months; acetyl L-carnitine was administered at the dose of 1 g/day for 4 months, while propionyl L-carnitine was administered at the dose of 500 mg/day for 4 months.

The combination according to the present invention significantly increases the sperm concentration and motility as well as the percentage of spermatozoa with a rapid linear progression as compared to treatment with the L-carnitine plus acetyl L-carnitine combination, regardless of the cause of the oligoasthenoteratospermia, even in patients with hormonal abnormalities.

In the latter, the combination according to the invention has permitted a reduction in the posology of gonadotropins and antiprolactinaemia drugs compared to the data reported in the literature.

The medicine according to the invention described herein can be prepared by mixing the active ingredients (L-carnitine inner salt, acetyl L-carnitine inner salt and propionyl L-carnitine inner salt or one of their pharmacologically acceptable salts) with suitable excipients for the formulation of compositions for enteral (particularly oral) or parenteral (particularly intramuscular of intravenous) administration. Experts in pharmaceutical technology are familiar with said excipients.

The pharmaceutically acceptable salts of the above-mentioned active ingredients include all the pharmaceutically acceptable salts that are prepared by addition of an acid to the L-carnitine, acetyl L-carnitine and propionyl L-carnitine inner salt, and that do not give rise to unwanted toxic or side effects. The formation of salts by addition of an acid is well known in pharmaceutical technology.

Examples of such salts, though not exclusively these, are: chloride, bromide, orotate, aspartate, acid aspartate, citrate, acid citrate, magnesium citrate, phosphate, acid phosphate, fumarate, acid fumarate, magnesium fumarate, glycerophosphate, lactate, maleate and acid maleate, mucate, oxalate, acid oxalate, pamoate, acid pamoate, sulphate, acid sulphate, glucose phosphate, tartrate, acid tartrate, magnesium tartrate, 2-amino ethane sulphonate, magnesium 2-amino ethane sulphonate, methane sulphonate, choline tartrate, trichloroacetate and trifluoroacetate.

The invention claimed is:

1. A method for the treatment of oligoasthenoteratospermia consisting of administering to a patient in need thereof an effective amount of a combination of L-carnitine, acetyl L-carnitine and propionyl L-carnitine inner salts or of their pharmaceutically acceptable salts, and suitable excipients.

2. The method according to claim 1, wherein oligospermia is treated.

3. The method according to claim 1, wherein asthenospermia is treated.

4. The method according to claim 1, wherein teratospermia is treated.

5. The method according to claim 1 in which the pharmaceutically acceptable salt is selected from the group consisting of chloride, bromide, orotate, aspartate, acid aspartate, citrate, acid citrate, magnesium citrate, phosphate, acid phosphate, fumarate, acid fumarate, magnesium fumarate, glycerophosphate, lactate, maleate and acid maleate, mucate, oxalate, acid oxalate, pamoate, acid pamoate, sulphate, acid sulphate, glucose phosphate, tartrate, acid tartrate, magnesium tartrate, 2-amino ethane sulphonate, magnesium 2-amino ethane sulphonate, methane sulphonate, choline tartrate, trichloroacetate and trifluoroacetate.

6. The method according to claim 1, in which a molar ratio of L-carnitine to acetyl L-carnitine and propionyl L-carnitine or of their pharmaceutically acceptable salts ranges from 2.48:0.098:0.092 to 0.186:0.98:0.92.

7. The method according to claim 1, in which a molar ratio of L-carnitine to acetyl L-carnitine and propionyl L-carnitine or of their pharmaceutically acceptable salts ranges from 2.48:0.49:0.46 to 0.62:0.49:0.46.

8. The method according to claim 1, in which a molar ratio of L-carnitine to acetyl L-carnitine and propionyl L-carnitine or of their pharmaceutically acceptable salts ranges from 2.48:0.98:0.92 to 1.24:0.49:0.23.

9. The method according to claim 1, in which the patient is administered a composition in unit dosage form which contains L-carnitine inner salt in amounts ranging from 4.0 g to 0.30 g, acetyl L-carnitine inner salts in amounts ranging from 0.20 to 2.0 g, and propionyl L-carnitine inner salt in amounts ranging from 0.20 to 2.0g, or equimolar amounts of their pharmaceutically acceptable salts.

10. The method according to claim 9, in which the unit dosage form contains 2 g of L-carnitine inner salt, 1 g acetyl L-carnitine inner salt and 0.5 g of propionyl L-carnitine inner salt or equimolar amounts of their pharmaceutically acceptable salts.

11. A method for the treatment of oligoasthenoteratospermia consisting of administering to a patient in need thereof an effective amount of a combination of L-carnitine, acetyl L-carnitine and propionyl L-carnitine inner salts, or of their pharmaceutically acceptable salts and suitable excipients, wherein the pharmaceutically acceptable salt is not zinc citrate.

12. The method according to claim 11 in which the pharmaceutically acceptable salt is selected from the group consisting of chloride, bromide, orotate, aspartate, acid aspartate, citrate, acid citrate, magnesium citrate, phosphate, acid phosphate, fumarate, acid fumarate, magnesium fumarate, glycerophosphate, lactate, maleate and acid maleate, mucate, oxalate, acid oxalate, pamoate, acid pamoate, sulphate, acid sulphate, glucose phosphate, tartrate, acid tartrate, magnesium tartrate, 2-amino ethane sulphonate, magnesium 2-amino ethane sulphonate, methane sulphonate, choline tartrate, trichloroacetate and trifluoroacetate.

13. The method according to claim 11, wherein oligospermia is treated.

14. The method according to claim 11, wherein asthenospermia is treated.

15. The method according to claim 11, wherein teratospermia is treated.

16. The method according to claim 11, in which a molar ratio of L-carnitine to acetyl L-carnitine and propionyl L-carnitine or of their pharmaceutically acceptable salts ranges from 2.48:0.098:0.092 to 0.186:0.98:0.92.

17. The method according to claim 11, in which a molar ratio of L-carnitine to acetyl L-carnitine and propionyl L-carnitine or of their pharmaceutically acceptable salts ranges from 2.48:0.49:0.46 to 0.62:0.49:0.46.

18. The method according to claim 11, in which a molar ratio of L-carnitine to acetyl L-carnitine and propionyl L-carnitine or of their pharmaceutically acceptable salts ranges from 2.48:0.98:0.92 to 1.24:0.49:0.23.

19. The method according to claim 11, in which the patient is administered a composition in unit dosage form which contains L-carnitine inner salt in amounts ranging from 4.0 g to 0.30 g, acetyl L-carnitine inner salts in amounts ranging from 0.20 to 2.0 g, and propionyl L-carnitine inner salt in amounts ranging from 0.20 to 2.0 g, or equimolar amounts of their pharmaceutically acceptable salts.

20. The method according to claim 19, in which the unit dosage form contains 2 g of L-carnitine inner salt, 1 g acetyl L-carnitine inner salt and 0.5 g of propionyl L-carnitine inner salt or equimolar amounts of their pharmaceutically acceptable salts.

21. A method for the treatment of oligoasthenoteratospermia consisting of administering to a patient in need thereof an effective amount of a combination of L-carnitine, acetyl L-carnitine and propionyl L-carnitine inner salts, or of their pharmaceutically acceptable salts and suitable excipients, wherein a molar ratio of L-carnitine to acetyl L-carnitine and propionyl L-carnitine or of their pharmaceutically acceptable salts ranges from 2.48:0.098:0.092 to 0.186:0.98:0.92.

22. The method according to claim 21, wherein oligospermia is treated.

23. The method according to claim 21, wherein asthenospermia is treated.

24. The method according to claim 21, wherein teratospermia is treated.

25. The method according to claim 21 in which the pharmaceutically acceptable salt is selected from the group consisting of chloride, bromide, orotate, aspartate, acid aspartate, citrate, acid citrate, magnesium citrate, phosphate, acid phosphate, fumarate, acid fumarate, magnesium fumarate, glycerophosphate, lactate, maleate and acid maleate, mucate, oxalate, acid oxalate, pamoate, acid pamoate, sulphate, acid sulphate, glucose phosphate, tartrate, acid tartrate, magnesium tartrate, 2-amino ethane sulphonate, magnesium 2-amino ethane sulphonate, methane sulphonate, choline tartrate, trichloroacetate and trifluoroacetate.

26. The method according to claim 21, in which a molar ratio of L-carnitine to acetyl L-carnitine and propionyl L-carnitine or of their pharmaceutically acceptable salts ranges from 2.48:0.49:0.46 to 0.62:0.49:0.46.

27. The method according to claim 21, in which a molar ratio of L-carnitine to acetyl L-carnitine and propionyl L-carnitine or of their pharmaceutically acceptable salts ranges from 2.48:0.98:0.92 to 1.24:0.49:0.23.

28. The method according to claim 21, in which the patient is administered a composition in unit dosage form which contains L-carnitine inner salt in amounts ranging from 4.0 g to 0.30 g, acetyl L-carnitine inner salts in amounts ranging from 0.20 to 2.0 g, and propionyl L-carnitine inner salt in amounts ranging from 0.20 to 2.0 g, or equimolar amounts of their pharmaceutically acceptable salts.

29. The method according to claim 28, in which the unit dosage form contains 2 g of L-carnitine inner salt, 1 g acetyl L-carnitine inner salt and 0.5 g of propionyl L-carnitine inner salt or equimolar amounts of their pharmaceutically acceptable salts.

* * * * *